(12) United States Patent
Nussey

(10) Patent No.: US 7,150,297 B2
(45) Date of Patent: Dec. 19, 2006

(54) METHOD AND APPARATUS FOR FILLING NEEDLELESS INJECTOR CAPSULES

(75) Inventor: Matthew Simon Nussey, Sheffield (GB)

(73) Assignee: Aradigm Corporation, Hayward, CA (US)

( * ) Notice: Subject to any disclaimer, the term of this patent is extended or adjusted under 35 U.S.C. 154(b) by 340 days.

(21) Appl. No.: 10/466,826

(22) PCT Filed: Jan. 25, 2002

(86) PCT No.: PCT/GB02/00329

§ 371 (c)(1),
(2), (4) Date: May 17, 2004

(87) PCT Pub. No.: WO02/060516

PCT Pub. Date: Aug. 8, 2002

(65) Prior Publication Data

US 2004/0199105 A1 Oct. 7, 2004

(30) Foreign Application Priority Data

Jan. 31, 2001 (GB) ................. 0102386.0

(51) Int. Cl.
B65B 31/00 (2006.01)

(52) U.S. Cl. ............... 141/7; 141/5; 141/8; 141/65; 141/286

(58) Field of Classification Search ............... 141/2–7, 141/31, 59–65, 57, 285, 286; 604/68–72, 604/232
See application file for complete search history.

(56) References Cited

U.S. PATENT DOCUMENTS 4,848,419 A * 7/1989 Damen ................. 141/61
5,725,032 A * 3/1998 Oshima et al. ........... 141/7

FOREIGN PATENT DOCUMENTS

DE 43 20 098 12/1994
WO WO 97/22375 6/1997

* cited by examiner

Primary Examiner—Timothy L. Maust
(74) Attorney, Agent, or Firm—Karl Bozicevic; Bozicevic, Field & Francis LLP

(57) ABSTRACT

A method is provided for filling needleless injector capsules with liquid drug, which eliminates or reduces trapped air bubbles in the drug. A two-stage vacuum method is disclosed which enables the capsule to be evacuated rapidly to very low pressure prior to filling. The method is also suitable for filling other small containers with liquids.

8 Claims, 6 Drawing Sheets

METHOD AND APPARATUS FOR FILLING NEEDLELESS INJECTOR CAPSULES

CROSS-REFERENCE TO RELATED APPLICATIONS

This application is a national phase of published PCT Application No. PCT/GB02/00329 filed Jan. 25, 2002 which claims priority to Great Britain Application No. 0102386.0 filed Jan. 31, 2001 both of which applications are incorporated herein in their entirety and to which applications is claimed priority.

BACKGROUND OF THE INVENTION

Needleless injectors are devices for delivery liquid drugs through the epidermis of a patient without using a conventional hypodermic needle. The normal principle of operation is to dispense a fine jet of liquid from a drug capsule at sufficiently high pressure and velocity to pierce the skin and deposit within the underlying tissues. The better designs of injectors usually have a two-phase injection pressure profile: the first is a very fast rise time from zero to a high pressure—typically in the region of 300 bars—which is the skin-piercing phase, followed by the remaining injectate at a lower pressure, which is sufficient to keep the hoke in the skin open during the injection. The high pressure is usually developed by a gas spring or pneumatic ram, or sometimes by pyrotechnic means.

Typically, the drug capsule is a cylinder with one end open, and the other having the injection orifice. A piston is located within the bore, and the drug is contained between the orifice and piston, the orifice being sealed temporarily by a rubber plug, cap or other known means.

Drug capsules are often made from a transparent thermoplastic, but at high strain rate these materials are brittle, and a problem that can occur during the high pressure phase is that the drug capsule can burst. It is possible to make the wall of the drug capsule sufficiently thick to withstand the burst pressure, but this may result in an unacceptably large device which is more difficult to make, and more expensive. This problem is exacerbated by the presence of bubbles of air trapped within the capsule after filling. This is th ought to be because of shock waves produced by the rapid collapse and expansion of the bubbles during the transition from the first and second pressure phases. The size of the bubble has an influence—those below about 2 microlitres volume having an insignificant effect. Larger bubbles, apart from the aforementioned problem, also compromise the accuracy of filing, so that an incorrect dose might be delivered. Another problem with some drugs, such as adrenaline, is that they are sensitive to the presence of oxygen, and it is necessary to reduce the volume of trapped air to a minimum.

Increasingly, it is preferred that the capsules are pre-filled by the manufacturers on specialized filling machines: this ensures good quality control, sterility, and traceability, and it follows from the foregoing that the volume of air trapped in the injectate should be as small as possible. Equally, low cost production demands high filling rates, typically less than 1 second for 1 ml fill volume. Current filling machines for both syringes and needleless injector capsules employ vacuum to reduce the amount of air trapped, but the vacuum systems operate at around 15 to 20 mbar or higher, which means that a significant amount of air remains in the syringe or capsule before the liquid drug in introduced. It is possible to design a vacuum system which can operate at lower pressure, but these require very large reservoirs, and consequently extended pump-down times and long filling cycles. It would be possible to avoid the use of reservoirs and to connect the capsule to be evacuated directly to a vacuum pump, but the final pressure, pumping times, and overall control, would be highly unsatisfactory except in the most crude applications.

SUMMARY OF THE INVENTION

The present invention is for a two-stage vacuum system which will rapidly evacuate needleless injector drug capsules, syringes and the like to low pressure prior to filling, without requiring cumbersome and inconveniently large reservoirs. In an advance over the prior art, there are provided reservoirs which may be connected sequentially to the capsule to be filled, so that the pressure within the capsule is lowered by pre-determined steps, in a highly repeatable manner, before filling.

According to the present invention there is provided a method of filling a needleless injector capsule with a material to be dispensed therefrom, which comprises connecting the capsule successively to at least a first reservoir at a sub-atmospheric pressure and a second reservoir at a sub-atmospheric pressure, and thereafter introducing the said material into the capsule.

In a preferred embodiment, there is provided a filling head which seals against the orifice of a drug capsule which has a piston or plunger already assembled therein, or otherwise has the open end sealed against the ingress of atmospheric air. Connected to the filling head is a vacuum system which first connects the capsule to a vacuum reservoir evacuated in 1 mbar; this raises the pressure of the capsule and reservoir to 15 mbar. This increased pressure within the combined reservoir and capsule would be too high to ensure minimal volume of trapped air within a filled capsule, and a second process stage isolates the first reservoir and connects the capsule to a second reservoir evacuated to 0.1 mbar. Since the capsule is already at a reduced pressure of 15 mbar, the resulting pressure in the order of 1 mbar is reached very quickly, and the capsule may be filled. A third process stage is to isolate both vacuum reservoirs and open the filling head to atmosphere to allow the capsule to be removed.

The volume of each reservoir is pre-determined in a fixed ratio to the volume of the capsule, connection pipes, valves and other ancillary equipment. One or more additional reservoir may be used and connected sequentially, and the pressures mentioned above are for illustration purposes only and may vary according to the application.

BRIEF DESCRIPTION OF THE DRAWINGS

The presently preferred embodiment will now be described with reference to the accompanying drawings, in which.

DETAILED DESCRIPTION OF THE PREFERRED EMBODIMENTS

Figure 1:
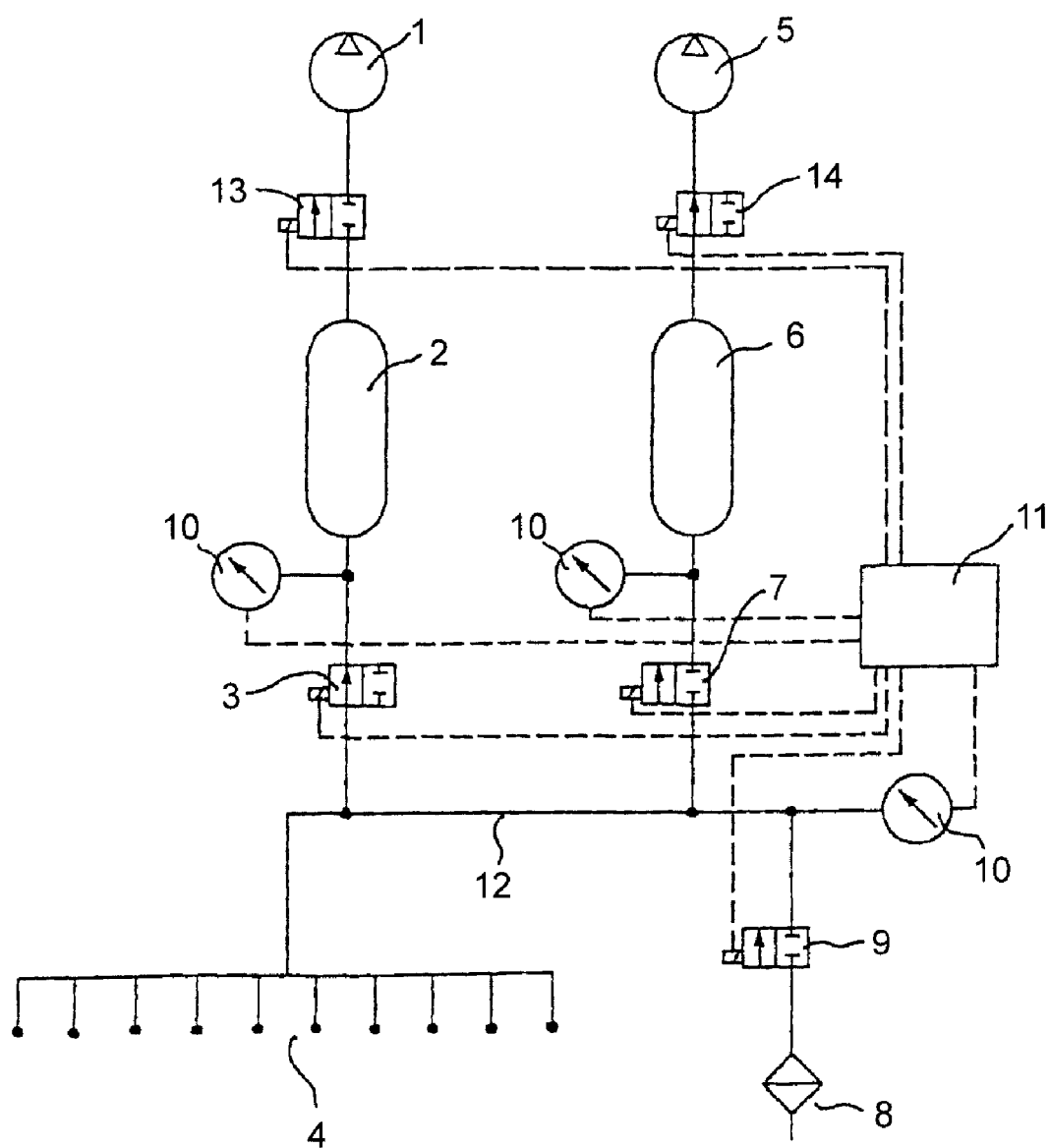
FIGS. 1, 2 and 3 show the evacuation sequence for a ten-head filler, (although the present invention is applicable to filling machines with any number of heads)

Referring to FIG. 1, the inlet of vacuum pump 1 is connected via an isolation valve 13 to reservoir 2, and the inlet of reservoir 2 is connected to a 2-port valve 3. Similarly, vacuum pump 5 is connected via isolation valve 14 to reservoir 5, the inlet of which is connected to the 2-port valve 7. The inlets of valves 3 and 7 are connected to the common vacuum bus 12. Connected to the vacuum bus 12 are the filling heads 4, and an air admittance valve 9. Transmitting gauges 10 are connected to the pipework to provide indications of the pressures during the filling cycle, and to transmit control signals to a sequence controller 11.

Figure 4A:
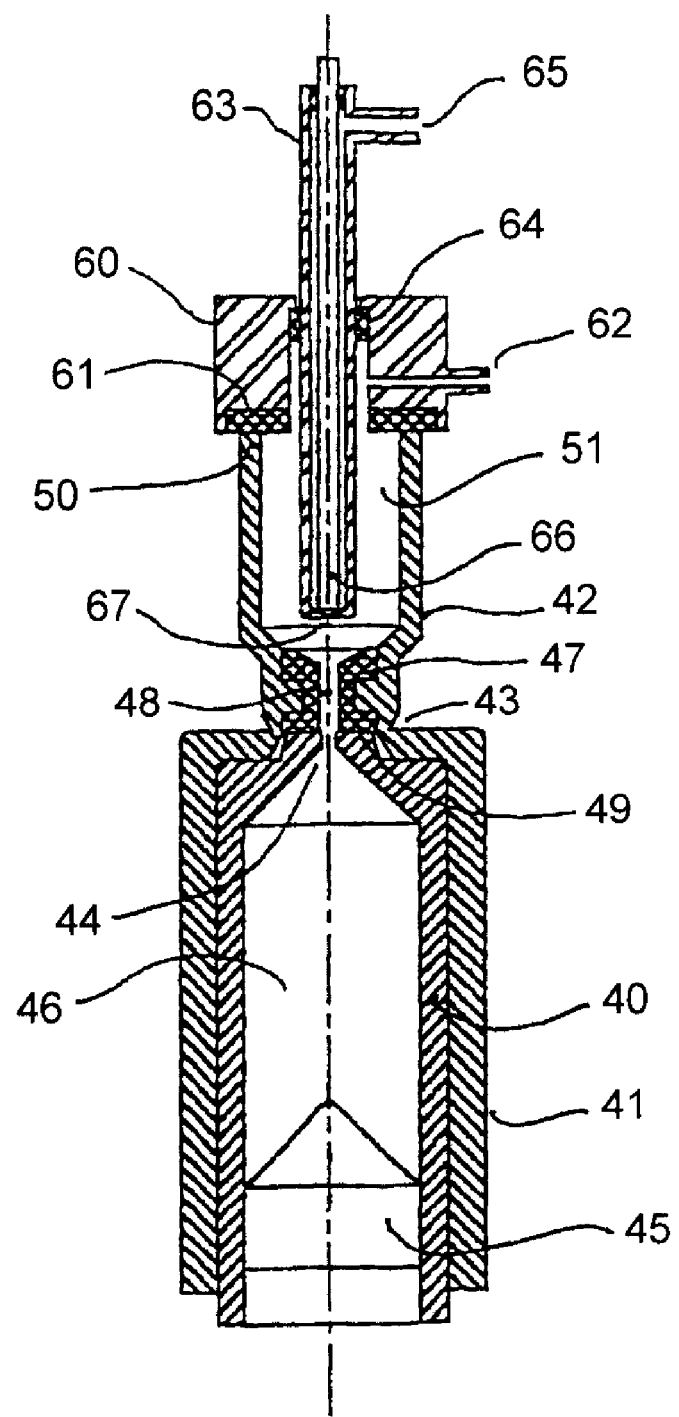
FIGS. 4*a*, 4*b* and 4*c* are centre-line cross sections through a suitable type of filling head an drug capsule of cylindrical form, to show the sequence of evacuation, sealing and filling.

Referring now to FIG. 4a, a capsule 40 is located with an interference fit within a sleeve 41. Sleeve 41 has a tubular extension 42, frangibly connected at 43, and the extension 42 has a resilient interface seal 47 fixed so that it forms a vacuum and liquid-tight seal on the face 49 of the capsule 40 and the inner surface of the extension 42. The seal 47 is perforated by a conduit 48 which is in hydraulic and vacuum connection with the injection orifice 44 of capsule 40. Sealingly and slidingly located within the bore of capsule 40 is a piston 45; its location is such that the volume 46 between the orifice and the piston is that which is required to be filled with liquid drug. A filling head 60 is shown sealingly engaged with the extension 42. The filling head 60 has a resilient seal 61 which makes a vacuum-tight seal between the head 60 and the rim 50 of the extension 42. A filling tube 63 is located for longitudinal sliding movement within a vacuum-right tube seal 64. The filling tube 63 is provided with a connection 65 for liquid input, and the filling head 60 is provided with a connection 62 for vacuum. A tip sealing valve 66 is shown sealing the outlet orifice 67 of the filling tube 64. FIG. 4a thus shows the position of the capsule and fling head components in a ready-to-evacuate state.

Figure 4B:
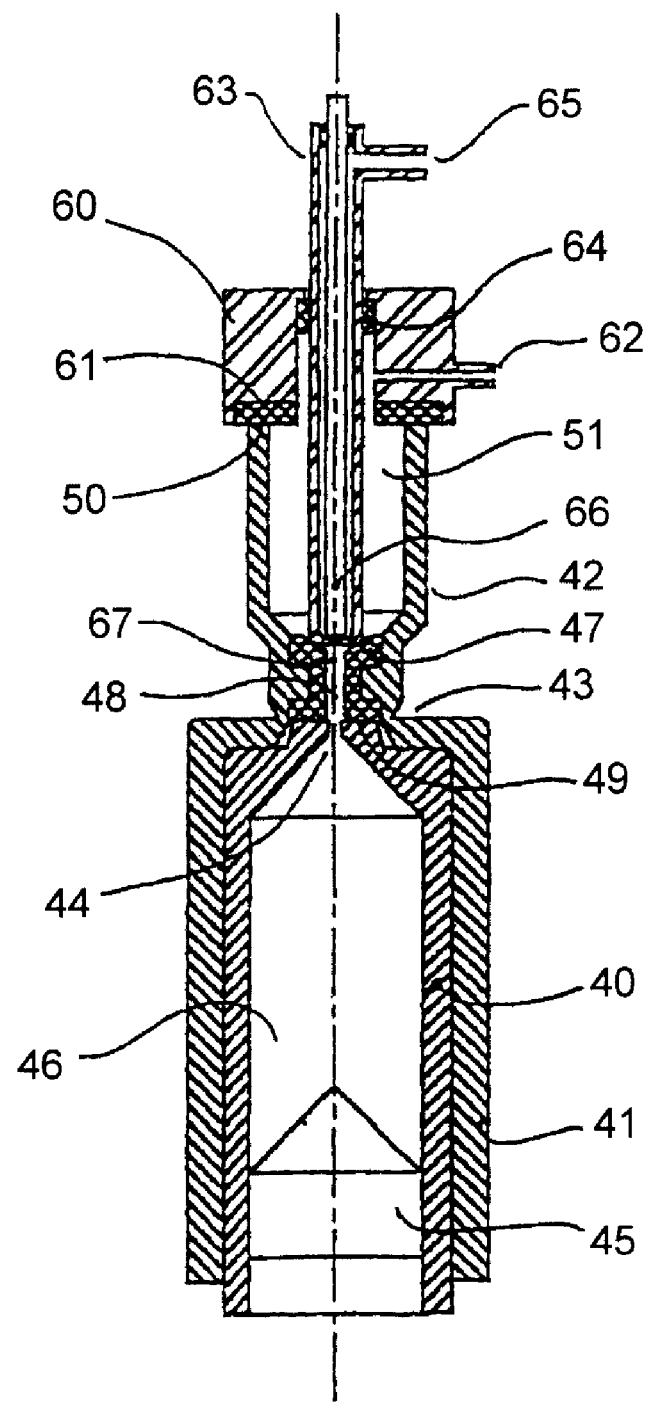

Referring to FIG. 4b, this shows the filling tube 63 located sealingly on the interface seal 47, so that the outlet orifice 67 is in vacuum and liquid-tight connection with the conduit 48. This is the position after evacuation of the capsule 40, and immediately prior to filling with liquid.

Figure 4C:
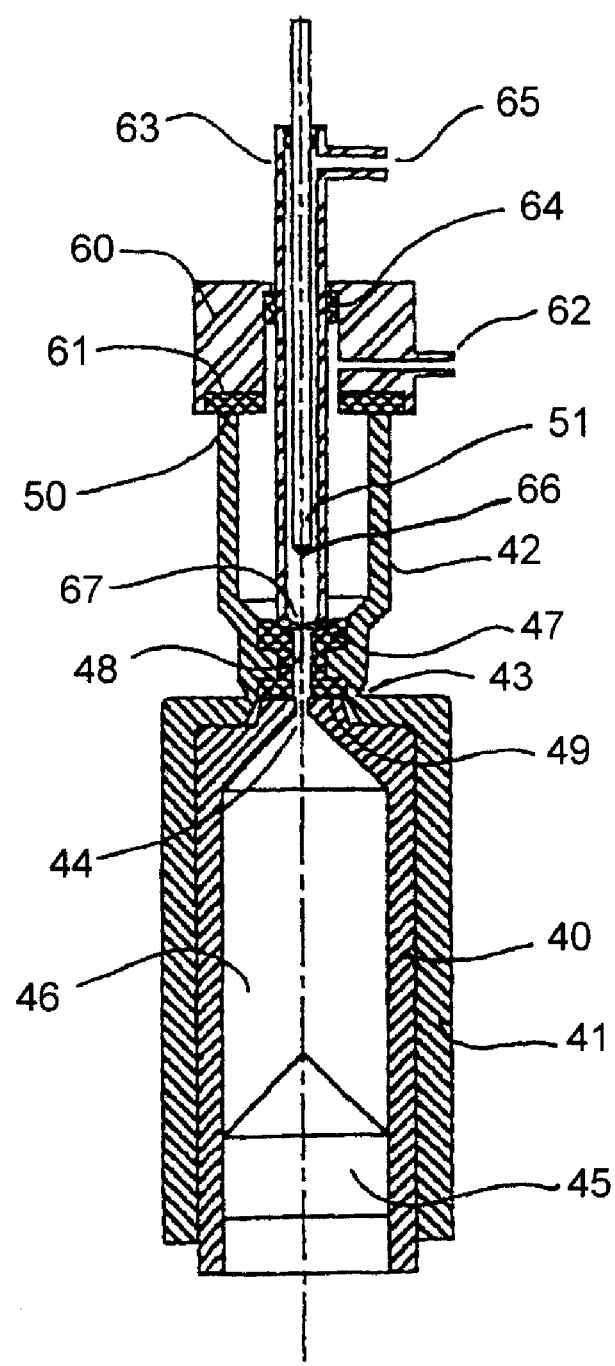

FIG. 4c is similar to FIG. 4b, except that the tip sealing valve 66 is lifted to open the outlet orifice 67. This permits liquid to flow from a liquid supply source (not shown) through connection 65, through the bore of filling tube 63, the outlet orifice 67, the conduit 48 and into the volume 46.

The filling sequence will now be described, starting by reference to FIG. 3. The approximate pressures achieved are for illustration only, and a calculated example will follow.

Stage 1

Figure 3:
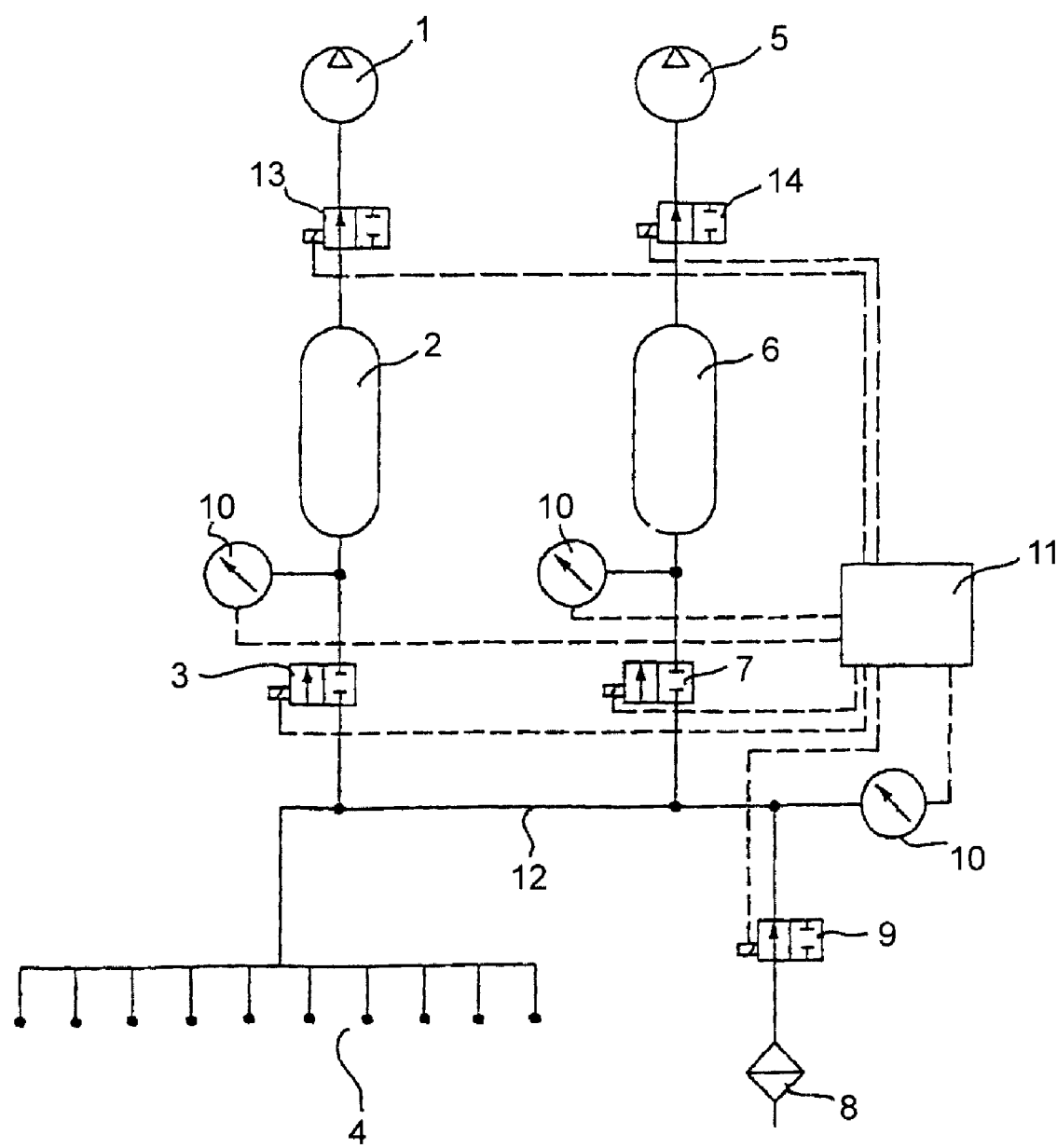

FIG. 3 shows diagrammatically ten filling heads and capsules 4 (which are as shown in FIGS. 4a, 4b and 4c) connected in parallel to the vacuum bus. Valve 9 is open, and thus connects the filling heads 4, via bus 12, to the atmosphere via filter 8. During this stage, valves 3 and 7 are closed, and the vacuum reservoirs 2 and 6 are being evacuated by pumps 1 and 5 respectively until the required vacuum is reached, when the valves 13 and 14 close to isolate the reservoirs 1 and 5. Reservoir 2 is evacuated to a pressure of 1 mbar, and reservoir 6 is evacuated to a pressure of 0.1 mbar by vacuum pump 5. Now, referring to FIG. 1, valve 9 is then closed, and valve 3 is opened, thus connecting the filling heads 4 to the reservoir 2 via bus 12. The filling heads and capsules are as shown in FIG. 4a. Note that the tip sealing valve 66 is closed to prevent the vacuum drawing out any liquid during the evacuation stage of the cycle.

Stage 2

Referring to FIG. 1, valves 9, 13, 14 and 7 are closed, and valve 3 is open, thus connecting the reservoir 2 to the filling heads 4 via bus 12. The atmospheric air which was contained in the bus 12 and filling heads 4 is therefore expanded to a lower pressure, dependent upon the ratio of the volume of reservoir 2 and the volume of the bus 12, filling heads 4 and any ancillary equipment such as the gauges 10, say 15 mbar.

Stage 3

Figure 2:
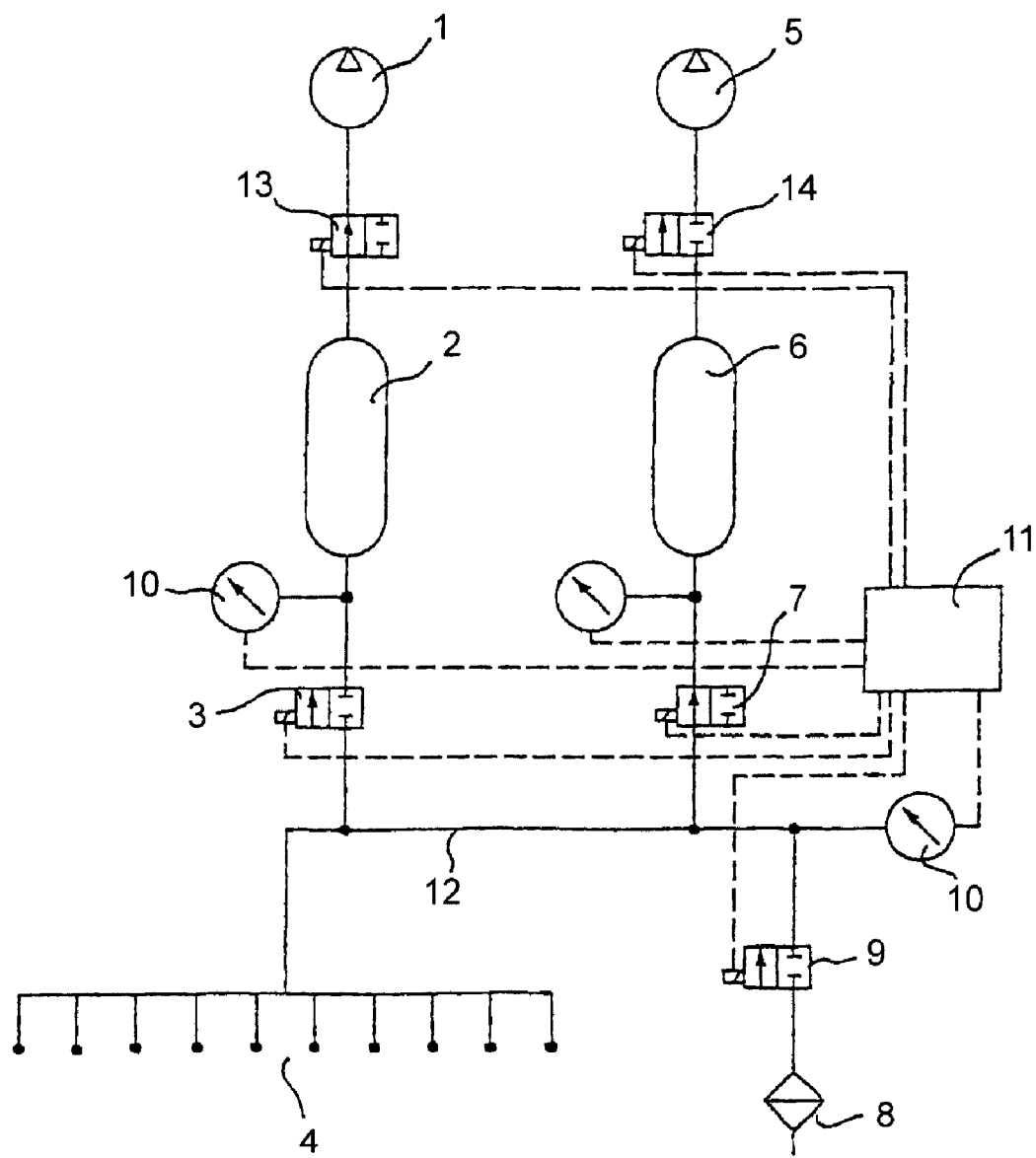

This stage reduces the pressure in the filling heads 4 as follows. Referring to FIG. 2, valve 3 is closed, after which valve 7 is opened, and this connects the filling heads 4 to the vacuum reservoir 6 via bus 12. Since the filling heads 4 and bus 12 are already at a reduced pressure of about 15 mbar from stage 2, there is a further reduction in pressure to about 1 mbar as the small amount of air in the system expands to fill reservoir 6. This expansion is very rapid—much less than one second for typical small volume containers. During this stage, the valve 13 may be open to evacuate the reservoir 2 ready for the next cycle.

When the pressure in the filling heads 4 is sufficiently low, referring to FIG. 4b, the capsule volume 46 and extension volume 51 are at a pressure of 1 mbar, and the outlet orifice 67 of filling tube 63 is now brought into sealing connection with the conduit 48 in the resilient interface seal 47. Liquid connection 65 is connected to a source of the liquid 52 (not shown) to be transferred to the capsule 40. The liquid 52 may be at above atmospheric pressure to overcome the resistance to flow of the filling tube 67 and associated pipework. As shown in FIG. 4c, the tip sealing valve 66 is now opened, and the liquid 52 thus flows into the volume 46. The pressure in the volume 46 was 1 mbar, so it follows that the maximum volume of air that could be trapped within the volume 46 is one thousandth of the said volume.

Stage 4

Following stage 3, the valve 7 may be closed to allow the reservoir 6 to be evacuated to the required level. With both valves 3 and 7 now closed, valve 9 is opened to connect the bus 12 and filling heads 4 to atmosphere—i.e. to release the vacuum. It is preferred in pharmaceutical filling operations to prevent airborne bacteria and other contaminants from reaching the various parts of the bus, valves and reservoirs, and the atmospheric air may be taken in via the filter 8. Referring to FIG. 4a, this is the position of each filling head 60 at the end of the evacuation and filling cycle. The head 60 is then removed from the extension 42 of capsule sleeve 41, and a sealing stopper or similar device is inserted into the bore of the extension 42 to seal against the ingress of dirt and bacteria, and to prevent loss of liquid by evaporation. Alternatively, a sealing pin may be inserted in the conduit 48. The filled capsule is removed, and the filling and sealing cycle is complete.

Transmitting gauges 10 inform the controller 11 that the correct conditions exist for each part of the sequence to begin. A number of safety devices such as pressure switches would be used in practical installations, but have been omitted from the description in the interests of clarity. Also, in a multiple filling head embodiment, it may be necessary to incorporate isolation valves to each head to prevent a malfunction in a filling head causing a massive air leak.

To avoid bubbles being formed in the liquid after filling according to the present invention, it may be necessary for the liquid to be de-gassed before filling.

As discussed, one of the objectives of the invention is to achieve predictable and repeatable pressures within the capsule prior to filling, and it may be seen from the fore going that by sequentially connecting the capsules to fixed volume reservoirs at known pressures, this objective may be achieved. As an illustration, the following is a calculated example of a typical installation, using the FIGS. 1 to 3 and 4a to 4c as references.

Pressures throughout are calculated using the ideal gas law equation:

$$PV = m/M\, R.T = v.R.T \quad (1)$$

NB v may be replaced by n
Where P=pressure exerted by gas (N/m$^2$)
V=volume of gas (m$^3$)
n=number of moles present in volume V $R$ = gas constant (kJ/kmole·K) or (kNm/kmole·k)

= 8.3144 kJ/kmole·K

T=temperature of gas K
Calculations involving vacuum usually quote pressures in mbar and volumes in liters, hence:
R becomes 83.14 mbar 0.1 . mole$^{-1}$. K$^{-1}$
Now with reference to FIG. 1,
Let P$_1$=pressure in reservoir 2
V$_1$=volume of reservoir 2
n$_1$=number of moles of air in reservoir 2
T$_1$=temperature of reservoir 1
P$_2$=pressure in reservoir 6
V$_2$=volume of reservoir 6
n$_2$=number of moles of air in reservoir 6
P$_3$=pressure in vacuum bus
V$_3$=volume of vacuum bus
(note that V$_3$=volume of pipes, gauges, valves and fittings)

Calculation of Vacuum Bus Volume V$_3$
Let volume of vacuum line connecting filler head+dead space in filler head=2 ml thus for 10 filling heads, volume is 2×10=20 ml=0.02 liters
Let volume 46 of capsule 40 and volume 51 of extension 42=1 ml, thus for 10 capsules is 1×10=10 ml=0.01 liters
Let the inside diameter of each filling head connecting tube be 500 mm, and the inside diameter be 3 mm. Thus the volume of 1 line is 3534 mm$^3$ and 10 lines is 10×3534=35340 mm$^3$=0.0353 liters
Let the volume of the vacuum bus be 0.0035 liters
Total volume V$_3$=0.0688 liters Then for Stage 1:
[1] number of moles in reservoir 2, n$_1$
Let P$_1$=1×10$^{-1}$ mbar V$_1$=5 liters T$_1$=293° K
P$_1$V$_1$=n$_1$RT$_1$ $$\therefore n_1 = \frac{1 \times 10^{-1} \cdot 5}{83.14 \times 293} = 2.05 \times 10^{-5} \text{ moles air}$$

[2] number of moles in vacuum system (or bus), V$_3$
Let P$_3$=1000 mbar V$_3$=0.07 liters $$\therefore n_3 = \frac{1000 \times 0.07}{83.14 \times 293} = 0.00287 \text{ moles air}$$

[3] On release of valve 3, total volume V$_3$ of the system is V$_1$+V$_3$ and therefore the total number of moles is n$_5$=n$_1$=n$_3$ Thus the system pressure P$_5$ after 1$^{st}$ stage vacuum is $$\frac{n_5 R T_5}{V_5} = \frac{(2.05 \times 10^{-5} + 0.00287) \times 83.14 \times 293}{(5 + 0.07)} \text{ mbar}$$

∴ pressure in the system after 1$^{st}$ stage evacuation is 13.9 mbar

Vacuum Stage 2
[4] Number of moles in reservoir 6: as V$_1$=V$_2$ and P$_1$=P$_2$, $$n_2 = n_1 = 2.05 \times 10^{-5} \text{ moles air}$$

[5] Number of moles n$_3$ remaining in vacuum system V$_5$ after 2$^{nd}$ stage:
now the pressure in the line P$_3$=P$_5$=13.9 mbar,
and the volume V$_3$=0/07 liters $$\therefore n_3 = \frac{P_3 V_3}{R T_3} = \frac{13.9 \times 0.07}{83.14 \times 293} \text{ moles air} = 4 \times 10^{-5} \text{ moles air}$$

[6] Number of moles in system, n$_5$:

$$n_2 + n_3 = 2.05 \times 10^{-5} \times 4 \times 10^{-5} = 6.05 \times 10^{-5} = 6.05 \times 10^{-5} \text{ moles air}$$

Thus the final pressure P$_{S2}$ after the 2$^{nd}$ stage evacuation (i.e. immediately before filling the capsule with liquid), is $$\frac{n_5 R T_5}{V_5} = \frac{6.05 \times 10^{-5} \times 83.14 \times 293}{5} = 0.29 \text{ mbar}$$

This is sufficiently low pressure to ensure that bubbles of air trapped within the liquid are insignificant. Note also that the calculations assume a perfect system with no leaks and outgassing; in practice very small leaks could occur, but the example given would be suitable for filling a 0.5 ml capsule with a maximum bubble size of about 0.5 μl.

The invention claimed is:
1. A method of filling a needleless injector capsule, comprising the steps of:
   connecting a needleless injector capsule to a first reservoir at a first sub-atmospheric pressure and thereby reducing an interior volume of the capsule to the first sub-atmospheric pressure;
   connecting the capsule to a second reservoir at a second sub-atmospheric pressure which is below the first sub-atmospheric pressure and thereby reducing the interior volume of the capsule to the second sub-atmospheric pressure; and
   introducing a liquid drug into the capsule.
2. The method of claim 1, further comprising:
   connecting the first reservoir to a source of sub-atmospheric pressure.
3. The method of claim 1, further comprising:
   connecting the second reservoir to a source of sub-atmospheric pressure.
4. The method of claim 1, further comprising:
   connecting the interior volume of the capsule to surrounding atmospheric pressure before connecting to the first reservoir and after introducing the liquid drug, wherein the interior volume of the capsule is connected to the surrounding atmosphere via a filter.

5. A method of simultaneously filling a plurality needleless injector capsules, comprising the steps of:

connecting a plurality of needleless injector capsules to a first reservoir at a first sub-atmospheric pressure and simultaneously reducing interior volumes of each of the plurality of the capsules to the first sub-atmospheric pressure;

connecting the plurality of capsules to a second reservoir at a second sub-atmospheric pressure which is below the first sub-atmospheric pressure and simultaneously reducing the interior volume of each of the plurality of capsules to the second sub-atmospheric pressure; and introducing a liquid drug into each of the plurality of capsules.

6. The method of claim 5, further comprising:

connecting the first reservoir to a source of sub-atmospheric pressure.

7. The method of claim 5, further comprising:

connecting the second reservoir to a source of sub-atmospheric pressure.

8. The method of claim 5, further comprising:

connecting the interior volume of each of the plurality of capsules to surrounding atmospheric pressure before connecting to the first reservoir and after introducing the liquid drug, wherein the interior volume of each of the plurality of capsules is connected to the surrounding atmosphere via a filter.

* * * * *